United States Patent [19]

Viggiano

[11] Patent Number: 4,713,055
[45] Date of Patent: Dec. 15, 1987

[54] ARTIFICIALLY VASCULARIZED GRAFT

[76] Inventor: Donato A. Viggiano, 1090 Virginia Ave., Ft. Pierce, Fla. 33450

[21] Appl. No.: 842,351

[22] Filed: Mar. 18, 1986

Related U.S. Application Data

[62] Division of Ser. No. 506,858, Jun. 22, 1983, abandoned.

[51] Int. Cl.⁴ .................... A61M 11/00; A61N 1/02
[52] U.S. Cl. .................................. 604/93; 435/1; 623/1
[58] Field of Search .............. 435/1, 2, 240; 604/93, 604/175; 623/1, 15

[56] References Cited

U.S. PATENT DOCUMENTS

| | | | |
|---|---|---|---|
| 3,883,393 | 5/1975 | Knazek et al. | 435/240 |
| 4,105,798 | 8/1978 | Moore et al. | 435/1 |
| 4,160,454 | 7/1979 | Foux | 604/93 |
| 4,184,922 | 1/1980 | Knazek et al. | 435/1 |
| 4,428,746 | 1/1984 | Mendez | 604/93 |
| 4,458,678 | 7/1984 | Yannas et al. | 623/15 |

OTHER PUBLICATIONS

Crawford B. The Management of Tube Pedicles, *Br J Plast Surg* 18:387, 1965.
Geyer R. Substitutes for Blood and its Components, *Prog Clin Biol Res* 19:1, 1977.
Baranowski J. Your Hematocrit is Zero, and You're Doing Fine, *Diag Med*:60, 1980.
Riess J. Perfluoro Compounds as Blood Substitutes, *Angew Chem Int Ed Engl* 17:621, 1978.
Sloviter H. Erythrocyte Substitute for Perfusion of Brain, *Nature* 216:458, 1967.
Toyohua, H. Isolated Heart Perfusion with FC-43: An Experimental Study, *Proceedings of the IVth International Symposium on PFC Blood Substitutes*, Kyoto, 1978.
Andjus R. An Isolated, Perfused Rat Brain Preparation, Its Spontaneous and Stimulated Activity, *J. Appl Physiol* 22:1033, 1967.
Shindo K. Experimental Studies on Kidney Preservation by Perfusion with Fluorochemical (FC-43) Emulsion at Room Temperature, *Proceedings of the IVth International Symposium on Perfluorochemical Blood Substitutes*, Kyoto, 1978.
Geyer R. Perfluorochemical Blood Replacement Preparations, *Proceedings of the IVth International Symposium on Perfluorochemical Blood Substitutes*, Kyoto, 1978.
Berkowitz H. Fluorochemical Perfusates for Renal Preservation, *J. Surg Res* 20:595, 1976.
Ohyanagi H. Experimental Studies on Kidney Perfusion with Perfluorochemical Emulsion in View of Graft Survival, *Proceedings of the IVth International Symposium on Perfluorochemical Blood Substitutes*, Kyoto, 1978.
Ohyanagi H. Clinical Studies of Perfluorochemical Whole Blood Substitutes: Safety of Fluosol-DA (20%) in Normal Human Volunteers, *Clin Therap* 2:306, 1979.
Tremper K. Hemodynamic and Oxygen Transport Effects of a Perfluorochemical Blood Substitute Fluosol-DA (20%), *Crit Care Med* 8:738, 1980.
Honda K. Clinical Use of Blood Substitute, *NEJM* 303:391, 1980.
Finseth F. An Experimental Neurovascular Island Skin Flap for the Study of the Delay Phenomenon, *Plast Recon Surg* 61, 412, 1978.
Guba A. Regional Hemodynamics of a Pedicle Flap: Evaluation by Distribution of Radioactive Microspheres, *J. Surg Re* 25:274, 1978.

*Primary Examiner*—C. Fred Rosenbaum
*Assistant Examiner*—Gene B. Kartchner
*Attorney, Agent, or Firm*—Eugene F. Malin

[57] ABSTRACT

Apparatus and method for temporarily keeping alive animal flaps or grafts by perfusing artificial blood initially through a tubular semi-permeable membrane including a plurality of capillaries and thereafter perfusing the artificial blood into the flaps or grafts.

23 Claims, 3 Drawing Figures

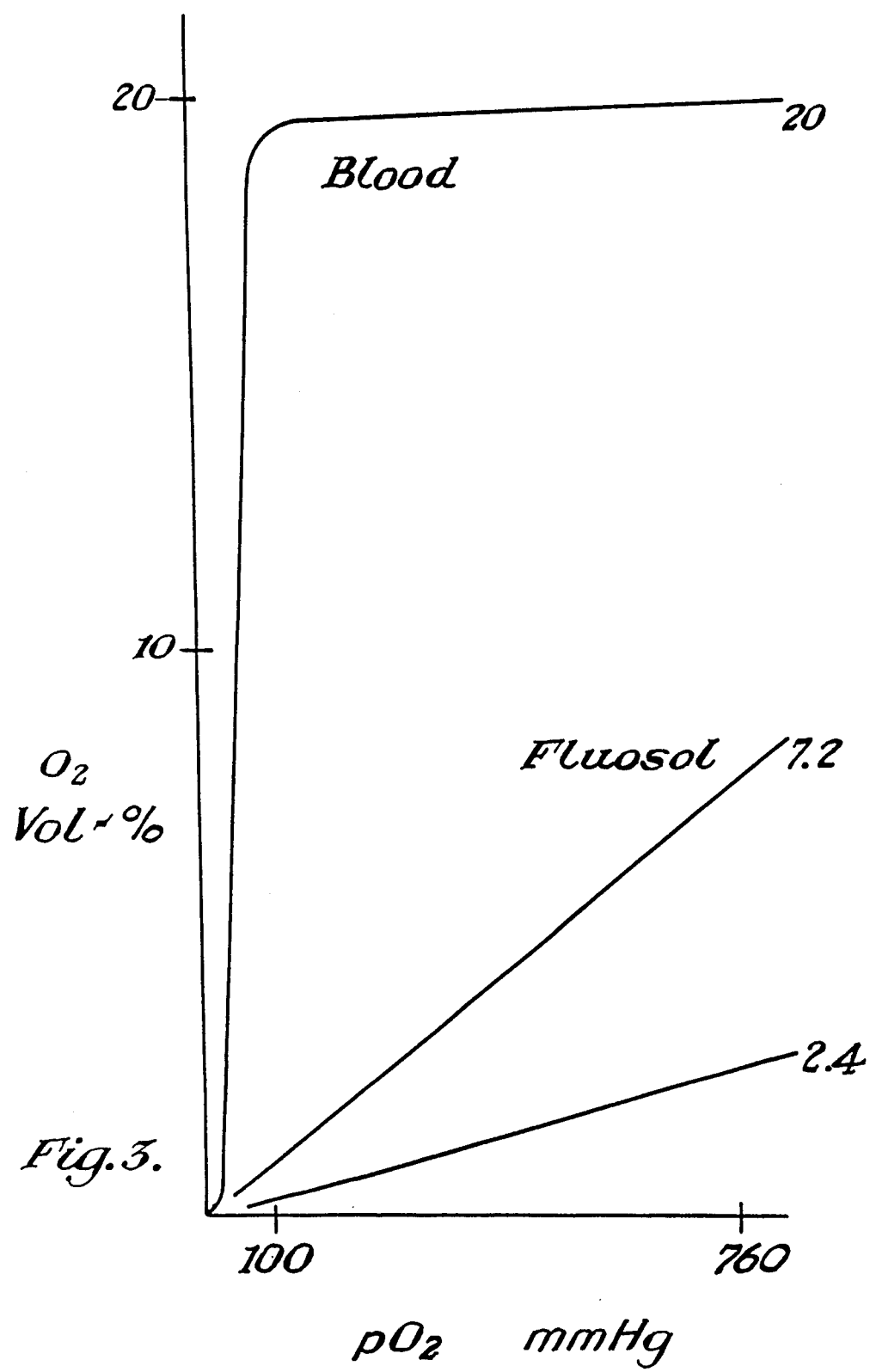

ARTIFICIALLY VASCULARIZED GRAFT

This application is a division of application Ser. No. 506,858, filed 6/22/83 now abandoned.

BACKGROUND OF THE INVENTION

Microvascular free flap technology provides a valuable means of transferring large flaps in one procedure, however, there are several major disadvantages. Microvascular free flaps are inappropriate for the reconstruction of small defects. The procedure is time-consuming and requires a skilled microvascular surgeon. Sufficiently large recipient vessels must be found. In addition, it is not uncommon to lose the flap from thrombosis of the anastomosed vessels.

It is known from past experience with tube pedicle flaps and cross leg flaps that the transferred flap is revascularized by the recipient bed in a relatively short time allowing for eventual transection of the pedicle, the distal part of the flap now supported totally by the recipient bed.

Artificial blood has heretofore been investigated for use in transfusion and organ preservation studies. Three types of artificial blood, i.e. free hemoglobin solutions, chelating agents, and perfluorocarbon emulsions have been investigated since the late 1960's in the preservation studies. Commercially available perfluorocarbon emulsion, Fluosol-DA 20 1/1 has been available for research purposes as it is capable of carrying large quantities of dissolved oxygen and carbon dioxide. This Fluosol emulsion is a mixture of perfluorodecalin and perfluorotripropylamine emulsified with Pluronic F68 and stabilized with egg yolk phosphatide. This emulsion is stored frozen until ready for use, at which time it is thawed and water, glycerol, solutes, glucose, and hydroxyethyl starch (an oncotic) are added.

DESCRIPTION OF THE PRIOR ART

U.S. Pat. No. 3,515,221 discloses apparatus for maintaining organs in a viable state for transplantation by perfusing a liquid through a cannula inserted into the blood vessel of an organ. The perfusate consists of a balanced salt medium containing dextran and sodium heparin buffered to a pH of 7.4 with tromethamine and sodium bicarbonate.

U.S. Pat. No. 3,734,851 which discloses a method and device for purifying blood by flowing animal blood over several semi-permeable membranes of a mixed esters of cellulose having an average pore size of 0.45 micron and a thickness of 150 microns. In one example of the invention a lyer of living liver cells are disposed between two of said membranes.

U.S. Pat. No. 4,186,565 discloses use of a membrane oxygenation in a portable preserving system using a perfusate.

LIST OF PUBLICATIONS

1. Converse J. *Reconstructive Plastic Surgery*. Philadelphia: Saunders, 1977. Chapter 86.
2. Crawford B. The management of tube pedicles. *Br J Plast Surg* 18:387, 1965.
3. Geyer R. Substitutes for blood and its components. *Prog Clin Biol Res* 19:1, 1977.
4. Baranowski J. Your hematocrit is zero, and you're doing fine. *Diag Med* :60, 1980
5. Riess J. Perfluoro compounds as blood substitutes. *Angew Chem Int Ed Engl* 17:621, 1978.
6. Sloviter H. Erythrocyte substitute for perfusion of brain. *Nature* 216:458, 1967.
7. Toyohua. H. Isolated heart perfusion with FC-43: an experimental study. *Proceedings of the IVth International Symposium on PFC Blood Substitutes*, Kyoto, 1978.
8. Andjus R. An isolated, perfused rat brain preparation, its spontaneous and stimulated activity. *J Appl Physiol* 22:1033, 1967.
9. Shindo K. Experimental studies on kidney preservation by perfusion with fluorochemical (FC-43) emulsion at room temperature. *Proceedings of the IVth International Symposium on Perfluorochemical Blood Substitutes*, Kyoto, 1978.
10. Geyer R. Perfluorochemical blood replacement preparations. *Proceedings of the IVth International Symposium on Perfluorochemical Blood Substitutes*, Kyoto, 1978.
11. Berkowitz H. Fluorochemical perfusates for renal preservation, *J Surg Res* 20:595, 1976.
12. Ohyanagi H. Experimental studies on kidney perfusion with perfluorochemical emulsion in view of graft survival. *Proceedings of the IVth International Symposium on Perfluorochemical Blood Substitutes*, Kyoto, 1978.
13. Ohyanagi H. Clinical studies of perflurorochemical whole blood substitutes: safety of Fluosol-DA (20%) in normal human volunteers. *Clin Therap* 2:306, 1979.
14. Tremper K. Hemodynamic and oxygen transport effects of a perfluorochemical blood substitute Fluosol-DA (20%). *Crit Care Med* 8:738, 1980.
15. Honda K. Clinical use of blood substitute. *NEJM* 303:391, 1980.
16. Finseth F. An experimental neurovascular island skin flap for the study of the delay phenomenon. *Plast Recon Surg* 61, 412, 1978.
17. Guba A. Regional hemodynamics of a pedicle flap: evaluation by distribution of radioactive microspheres. *J Surg Re* 25:274, 1978.
18. Pinggera W. The fiber dialyzer. *J Extra-Corporeal Tech* 4:6, 1871.
19. Gotch F. Chronic hemodialysis with the hollow fiber artificial kidney (HFAK). Trans Amer Soc Artif Intern Organs 15:95, 1969.

SUMMARY OF THE INVENTION

This invention relates to the use of perfluorocarbon emulsions, particularly, Fluosol-DA 20%, an artificial blood, for temporary tissue support of non-microvascular free flaps for keeping alive the flaps via an external circuit for a required time for revascularization thereby permitting transfer of the flap without a pedicle. The term "flap" as used herein is considered synonymous to a graft.

This invention further relates to the utilization of a cellulose matrix including a plurality of tubules of micron size as a tubular semi-permeable membrane disposed in direct contact with a viable tissue through which the fluorocarbon emulsion perfuses through prior to profusing into the flap or graft.

One advantage of the invention using perfluorcarbon emulsion perfusion is decreased operative time or the need for a skilled microvascular surgeon when utilizing microvascular techniques.

Another advantage of the invention is obviating the requirement for a searching for appropriate recipient vessels.

Still another advantage by the use of perfluorocarbon emulsions is in negating loss of flap from thrombosis since these emulsions do not clot.

Still another advantage of the invention is elimination of the need for dissection and canulation of the vessels in the flap and negation of loss of artificial blood by use of the cellulose semi-permeable membrane.

BRIEF DESCRIPTION OF THE DRAWING

FIG. 3 graphically shows Vol. % $O_{2v}.pO_2$ in blood, Fluosol, and water.

DETAILED DESCRIPTION OF THE INVENTION

The invention relates to a system for keeping alive a flap or graft by perfusion of a fluorocarbon emulsion into the flap or graft as more fully described below.

A tubular semi-permeable membrane is obtained from a Cordis Dow 1.8D hemodialysis unit. Each unit includes over 13,000 tubules made of a thin-walled cellulose matrix, the internal diameter of the tubules is 200 microns with a wall thickness of 30 microns.

The perfluorochemicals in Fluosol-DA 20% set forth in Table 1 below, are emulsified for aqueous suspension into particles approximately 0.4 micron in diameter. These particles would not be expected to cross the tubular semi-permeable membrane described above. Thus the emulsified perfluorochemicals remain completely separate from the tissue during the flap perfusion studies.

TABLE 1

| COMPOSITION OF FLUOSOL-DA | |
|---|---|
| Perfluorodecalin | 14.0 W/V % |
| Perfluorotripropylamine | 6.0 W/V % |
| Pluronic F68 (emulsifier) | 2.7 W/V % |
| Yolk phospholipids (stabilizer) | 0.4 W/V % |
| Glycerol | 0.8 W/V % |
| NaCl | 0.48 W/V % |
| KCl | 0.027 W/V % |
| $MgCl_2$ | 0.015 W/V % |
| $CaCl_2$ | 0.022 W/V % |
| $NaHCO_3$ | 0.168 W/V % |
| Glucose | 0.144 W/V % |
| Hydroxyethyl starch (oncotic) | 3.0 W/V % |
| pH: 7.4–7.6 | |

Figure 2:
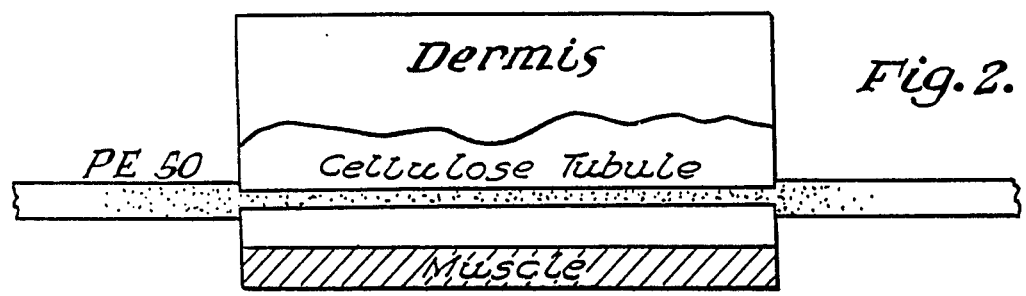
FIG. 2 illustrates an enlarged view of a tubular semi-permeable membrane placed parallel to the skin surface between the dermis and muscle.
Figure 1:
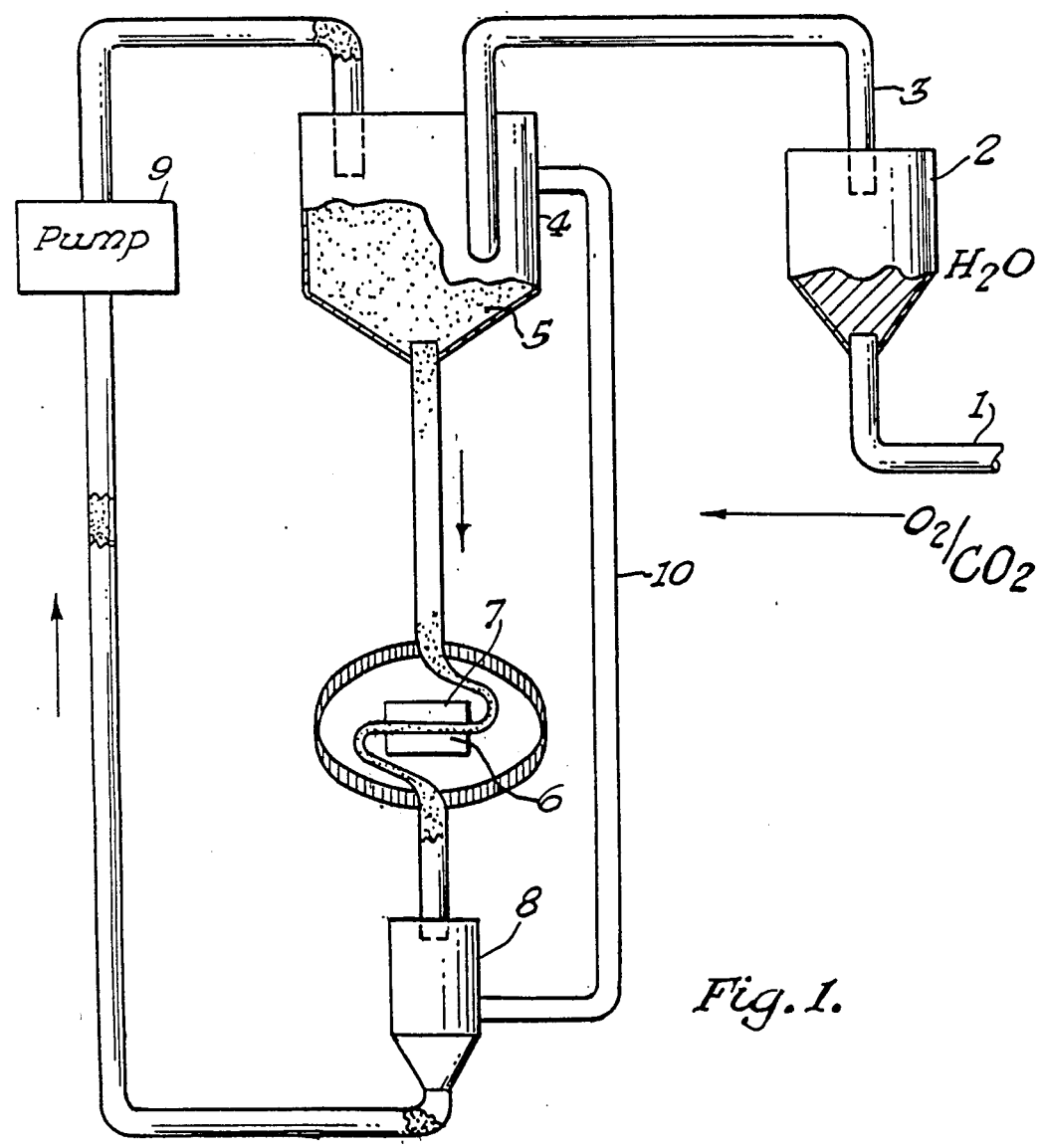
FIG. 1 illustrates a circulatory system for keeping a flap or graft alive for surgical purposes of the invention.

PE 50 polyethelene tubing functions as an artificial capillary or "artery" and "vein" for delivering the perfuorocarbon emulsion to the tubular semi-permeable membrane. The tubular semi-permeable membrane was inserted within the polyethelene tubing for a distance of about one to two centimeters and adhesively secured in place with cyanoacrylic glue. The "arterial" side was secured preoperatively and then gas sterilized. When a flap of a rat was raised, a 23 gauge needle was placed within the flap through which was placed the artificial capillary. See FIG. 2. The needle was then removed. The artificial capillary was then placed about 1–2 cm inside a second length of sterile PE 50 polyethelene tubing acting as a "vein" and was glued in place with gas-sterilized cyanoacrylic glue. The polyethelene tubing was then sutured to the flap or graft to minimize traction on the glued connection. The artificial blood was oxygenated by feeding a mixture of 95% $O_2$/5% $CO_2$ through conduit 1 into vessel 2 containing water to humidify the mixture which is then introduced into a 50 cc large reservoir 4 containing artificial blood 5 as shown in FIG. 1. Delivery pressure was controlled by gravity feed to be 100 cm $H_2O$, the approximate mean arterial blood pressure in the rat. The artificial blood then went through a 20 micron filter 6 and into the flap 7. From the flap, the artificial blood then entered a 30 cc smaller reservoir 8 and was recycled by pump 9 to the reservoir 4. The bubbles of $O_2/CO_2$ mixture were allowed to escape reservoir 4 via an overflow tubing 10 to the lower reservoir. From the lower reservoir, it was vented at the top of smaller reservoir 8 into the atmosphere. The hollow cellulose fiber of a Cordis Dow hemodialysis unit is used as the artificial capillary and eliminates the need for dissection and cannulation of vessels. Consequently, potential donor sites are unrestricted. The flap can be as small or as large as desired simply by adding more artificial capillaries as needed. No loss of artificial blood into the tissue occured since it remained in the artificial capillary and external circuit. Finally, since the artificial capillary was relatively large, embolized air passed freely through it and did not halt the perfusion.

In the invention described above four flaps were maintained in vitro using the Perfluorocarbon emulsion tissue (PET) support technique. After seven days of perfusion, the perfused flaps were histologically indistinguishable from freshly harvested skin and muscle, while a control non-perfused flaps showed advanced necrosis.

A 5×5 cm flap can be supported in its entirety by one tubule since enough diffusion of nutrients and waste products occurred over the 2.5 cm so that the tissue remained viable. The nutrient concentration of the perfluorocarbon emulsion is such that it is substantially the same as in arterial concentrations.

The capillaries described above were also embedded into the free flaps or grafts and perfused with fluorosol for seven (7) days and incubated at 98 degrees F. At the end of this time, the perfluorocarbon emulsion tissue supported skin and muscle flaps were histologically indistinguishable from freshly harvested skin and muscle.

To establish the superiority of the invention, tests have been conducted including absence of semi-permeable membranes and use of a polyethylene semi-permeable membrane as set forth below.

In these tests the tissue vasculature was used. The perfluorocarbon emulsion flowed into the artery and out the vein of a free axial pattern flap of an animal, e.g. rat.

Female Sprague Dawley rates were used (250–350 grams). All rats were anesthetized for surgery with Ketamine (87 mg/kg) and Zylazine (13 mg/kg) IM. The surgery was performed using aseptic technique.

Test I Vascular Tree

A. Axial Intact Group-Ten Rats

The inferior epigastric flap was used. The axial pattern flap was elevated superficial to the abdominal wall fascia and incorporated the panniculus carnosis. The flap measured 8 cm from xiphoid to pubis and 4 cm from umbilicus to the lateral change from thin abdominal skin to thick dorsal skin. The superior margin followed the rib cage and the inferior margin included the inguinal fat pad. The medial border was the abdominal midline.

The inferior superficial epigastric artery and vein were left intact but the accompanying nerve was cut. The flap was sutured back in place with 5-0 steel.

B. Axial Ligated Group-ten rats

The inferior epigastric flap was raised as before but this time the inferior superficial epigastric vessels were ligated along with the accompanying nerve transection. The flap was sutured in place with 5-0 steel.

C. Blood Flow Estimation Group-two rats

In two rats the flap was raised as before and sutured loosely to its bed. The inferior superficial epigastric vessels were left intact. Radioactive microspheres were injected in the left ventricle via the right carotid artery. Shortly before, during, and shortly after the microsphere injection blood was withdrawn at the constant rate of 0.42 cc/min. from the left iliac artery. The radioactivity of the sample of blood was compared to the radioactivity of the raised flap. The blood flow to the flap was calculated using the formula:

Blood flow to the flap−0.42 cc/min.=Radioactivity count of flap−Radioactivity of blood sample.

D. Axial Perfusion Group-fifteen rats

The flap was raised as before. The nutrient inferior superficial epigastric artery and vein were transected and cannulated with PE 10 polyethelene tubing. The flap was removed from the rat and placed in a petri dish bathed in Euro-Collins Solution (see Table 2):

TABLE 2

| Ingredients of Euro-Collins Solution per 100 cc | |
|---|---|
| Dibasic Potassium Phosphate Anhydrous USP | 740 mg |
| Monobasic Potassium Phosphate, NF | 205 mg |
| Potassium Chloride, USP | 112 mg |
| Sodium Bicarbonate, USP | 84 mg |
| Glucose (added) | 5 mg |
| pH 7.2 | |

(This solution is an approximation of intracellular fluid)

Perfusion of the artery and vein was attempted with the perfluorocarbon emulsion Fluosol-DA 20%.

E. Axial Delay Group-two rats

The flap was raised as before with the artery and vein left intact and the nerve transected. The flap was satured in place with 5-0 steel. At seven days in one rat and at nine days in the other, the axial vessels were ligated through a small groin incision.

Experiment II Artificial Capillary

A. Back Control Group-ten rats

A 2×2 cm square of skin and panniculus carnosus was elevated from the rat's back. The flap was taken in the midline, 10 cm from the occiput. After being completely detached from the rat, it was reversed so the hair was oriented toward the head and sutured in place with 5-0 Silk.

B. In Vitro Back Group-five rats

A square of skin and panniculus carnosus was elevated from the rat's back as described above. Three 2×2 cm square flaps were raised, one 3×3 cm flap and one 5×5 cm flap. Within these flaps, tubular semipermeable membranes were placed parallel to the skin surface between the dermis and muscle. PE 50 polyethelene tubing acted as the "artery" and "vein" (see FIG. 2). The Table 3 shows the number and spacing of the tubules in each flap. Each flap was placed in a covered petri dish, raw surface down, bathed in a Euro-Collins Solution in which was added Penicillin G 100,000 u/L. The flap was then placed in an incubator at 98 degrees for seven days. Histologic sections were then taken for H and E staining.

TABLE 3

| In Vitro Back Flap Trials | | |
|---|---|---|
| Back Flap | # of Tubules | Spacing of Tubules |
| 2 × 2 cm | 4 | 4 mm |
| 2 × 2 cm | 2 | 6 mm |
| 2 × 2 | 1 | — |
| 3 × 3 | 1 | — |
| 5 × 5 | 1 | — |
| 2 × 1/3 × 1/5 × 1 cm | none (control) | — |

Oxygenated Fluosol-DA 20% was perfused through the tubules for the entire seven days. A control flap of skin and muscle was placed in a separate petri dish for each trial run and treated in the same way as the trial flap except that no tubule was placed and no Fluosol-DA 20% was perfused. The Euro-Collins Solution bath was drained and replaced everyday using sterile technique. The Fluosol-DA 20% and the oxygenation and pumping system tubing and reservoirs were replaced at three days with an identical fresh system.

C. In Vivo Back Group-fifteen rats

A 2×2 cm square of back skin and panniculus carnosus was completely elevated as before. One tubular semi-permeable membrane was placed transversely through the flap as in the vitro study. The flap was returned to the rat in reverse position so the hair was oriented toward the head. The PE 50 polyethelene tubing was tunneled to the nape of the neck where it entered the rat as the "artery" to the artificial capillary. From the other side of the artificial capillary a second polyethelene tubing was tunneled to the chest where it exited as the "vein." The Fluorosol-DA 20% perfusion was run as long as possible in an attempt to perfuse the flap for seven days. The Fluosol, tubing and reservoirs were again replaced at three days.

Rats cannot be immobilized for long periods of time without gastric ulceration and hemmorhage. Therefore, in order to protect the polyethelene catheters and allow for freedom of movement, stainless steel harnesses were attached to the chest and the nape of the neck with polyethelene bolts. The polyethelene tubing passed through the harnesses and entered a steel spring sheath. One sheath connected the nape of the neck to a swivel connector placed over the cage, another sheath connected the chest to a second swivel connector placed beneath the cage. These swivel connectors were specially made to allow for rotation of this tubing and sheath without undue tension on or twisting of the tubing.

RESULTS

Test I

A. Axial Intact Group: All flaps remained completely viable.

B. Axial Ligated Group: All flaps necrosed entirely. The flaps clinically remained unchanged until approximately day three. The flap was then noticeably darker and within several days it became frankly necrotic and was shed.

C. Blood Flow Estimation Group: In one rat the radioactivity count of the blood sample was 887 and the flap 447. In the second rat the counts were 960 and 482. This gives an average estimated blood flow of 0.2 cc/min to the flap in the anesthetized rats. (Each flap measured approximately 31 cm 2. The blood flow is calculated to be 0.007 cc/min/cm 2.)

D. Axial Perfusion Group: Cannulation of the inferior superficial epigastric vessels was difficult and rupture of the vessels was common. Attempted perfusion after vessel rupture caused immediate swelling of the areolar tissue and eventual perfusion stoppage. Eight flaps failed to be perfused in this way. Four flaps could not be perfused sufficiently to get an adequate venous return. Three flaps were perfused with adequate venous return but this was not sustained for more than two hours in any flap. At no time was the return flow rate greater than 0.1 cc/min. (Compare to estimated blood flow rate of 0.2 cc/min from the microphere studies).

E. Axial Delay Group: 80% of the flap survived subsequent ligation of the pedicle after seven days of revascularization and 85% after nine days as determined by the paper template method.

Test II Artificial Capillary

A. Back Control Group: All grafts necrosed. Discoloration was apparent on day five with frank necrosis noted on day twelve. Most grafts were shed by day sixteen.

B. In Vitro Back Group: All control flaps showed histologic changes consistent with advanced necrosis. Collagen staining in the dermis was diminished and there was evidence of disruption of the collagen matrix. The muscle layer showed disintegration of the fascicles and fragility to the staining process. On day two the 2×2 cm flap perfused with one tubule had three colonies of similar organisms, the largest of which grew directly over the tubule. These colonies were removed and the flap washed with the Euro-Collins Solution. The following day the perfusion was found to have stopped when the colonies had returned. The colonies were much greater in size, the one over the tubule, the largest, having digested into the flap and into the tubule. The perfluorocarbon emulsion had flowed out through the disruption and into the petri dish. This flap was excluded from the study. All the remaining flaps were perfused continuously for the full seven days. H and E stained histology at the end of seven days revealed normal architecture and staining characteristics. The dermal collagen was well organized and deeply stained. The muscle layer showed the normal peripheral nucleii and striations. As expected, there was no inflammatory response seen. A light blue staining of the collagen within 15 to 20 microns of the tubule was noted.

C. In Vivo Back Group: Despite the stainless steel harnesses, circular cages and swivel connectors, all but one of the rats were able to disrupt the perfusion in the first few days. This usually occurred as the rat awoke from anesthesis but in two cases disruption occurred at two days. The perfluorocarbon emulsion flowed out of the circuit and into the wound in all cases.

The flap was perfused for seven days in one rat. Unfortunately, the perfusion in this rat was not continuous. Interruptions of flow for up to three and four hours were common. In one instance, there was no perfusion for an estimated four to six hours. This occurred on day five. Usually the perfusion could be restarted using a normal saline flush. In two instances, the swivel connectors were clogged to such an extent that they had to be replaced with fresh connectors.

At one week, the control non-perfused grafts were discolored and eventual shedding of the graft could be anticipated. The perfused flap at one week, the end of the perfusion, looked entirely normal. By two weeks, most control flaps had been shed. The perfused flap was discolored and firm in its periphery but still intact. It did not look very much different from the control grafts at one week. By three weeks most controls had almost healed their ulcers. The perfused flap had begun to ulcerate and was totally shed by 22 days. (See Table 4 below).

TABLE 4

|  | Control Composite Graft | Perfused Flap |
|---|---|---|
| Discoloration | 3–5 days | 10 days |
| First Ulceration | 12–15 | 20 |
| Complete Ulceration | 14–17 | 22 |
| Clinical appearance of back graft/flap | | |

DISCUSSION

Test I Vascular Tree

It was impossible to perfuse the free axial pattern flap selected as the model in this experiment. The inferior superficial epigastric vessels, which supply the inferior epigastric flap, are small delicate vessels in the rat. Cannulation was difficult and post-traumatic rupture common. High perfusion pressures were needed to get what flow was obtained, and as expected, this increased the likelihood of vessel rupture. The 0.2 cc/min flow rate to the inferior epigastric flap as determined by the microsphere study was not obtainable. Preopertive heparinization (50 units/kg IV) of the rat did not improve the poor flow rate.

Further research into the use of the tissue's own vascular tree as the delivery system for the artificial blood was abandoned for several reasons. If larger vessels were indeed necessary for adequate perfusion, then possible donor sites and flap size would be similar to that of microvascular free flaps. Dissection of the donor vessels would be the same as in the microvascular technique. Cannulation of the vessels, through easier than anastomosing them, is none the less difficult and exacting. In addition, the emulsion may leak out into the cut ends of the flap, in other words, bleed artificial blood, or may enter the host's vascular system as the revascularization of the flap progressed. Finally even a small amount of air embolization could immediately stop the flow permanently.

Test II The Artificial Capillary

The use of an artificial capillary was used to overcome the problems encountered with using the tissue's own vascular recipient bed is closer to that of the post-capillary (venous) rather than the pre-capillary (arterial) concentration. Also, in the clinical situation there is undoubtedly some interference with the diffusion by microhematoma formation in the graft-recipient bed interface. The nutrient concerntration of the perfluorocarbon emulsion is closer to arterial concentrations. For example, the calculated $PO_2$ of the perfluorocarbon emulsion equilibrated with 95% $O_2$ is 724 torr compared with 40 torr for venous blood. Since there is no blood flow in the detached flap, a hematoma between the flap tissue and the tubule would be unexpected.

Perfusion of the flap using the artificial blood/artificial capillary system (PET Support) was technically difficult in the in vivo rat model. Great pains were taken to protect the perfusion set-up from interference by the rat, but this was rarely possible. Disruption of the perfusion in the first few days was common. These perfusions did not support the free flap long enough to draw any conclusions as to the efficacy of PET Support in vivo.

In one rat the PET Support of the flap did last the required seven days. No biopsy of this flap was taken, so the vitality of the flap at the end of the perfusion could not be proven. Although the perfusion was discontinuous for four or five hours on Day 5 of the trial, the flap behaved as though its ischemic insult began at about the tree as the delivery system.

Perfusion of the flap using the artificial blood/artificial capillary system (PET Support) was technically difficult in the in vivo rat model. Great pains were taken to protect the perfusion set-up from interference by the rat, but this was rarely possible. Disruption of the perfusion in the first few days was common. These perfusions did not support the free flap long enough to draw any conclusions as to the efficacy of PET Support in vivo.

In one rat the PET Support of the flap did last the required seven days. No biopsy of this flap was taken, so the vitiality of the flap at the end of the perfusion could not be proven. Although the perfusion was discontinuous for four or five hours on Day 5 of the trial, the flap behaved as though its ischemic insult began at about the time the perfusion was halted at seven days.

The eventual loss of the PET Support flap can be explained in several ways. First, the perfusion was not continuous over the seven day period due to technical difficulties. This alone may have allowed early necrosis of the flap. Second, it can be postulated that a period of time longer than seven days may be necessary for vascular ingrowth, especially since the PET supported flap probably had a relatively $PO_2$ and low waste product concentration. Lacking these known stimulants for angiogenesis, the ingrowth of blood vessels may have been inhibited. It is also unknown what effect the lack of amino acids, vitamins, hormones and an active immune system had on the perfused flap and its ability to become revascularized.

PET Support has potential uses that could revolutionize the practice of Plastic Surgery. In addition to tissue transplantation, as in the non-necrovascular free flap, PET Support may also prove valuable in healing studies, in repair of avulsion injuries, such as the ear or nose, and in the salvage of failing conventional flaps.

The perfluorocarbon emulsion, Fluosol-DA 20%, a commerically available artificial blood substitute was used to nourish free flaps or graft in the rat model.

Two delivery systems were investigated, the tissue vasculature of a free axial pattern flap and a tubular semi-permeable membrane acting as an artificial capillary.

Adequate perfusion of the free axial pattern flap (the inferior epigastric flap), could not be accomplished. Since the artificial blood could not be perfused, it remains unanswered as to whether it could maintain the viability of this or any other free axial pattern flap.

It is to be understood that various changes may be made in the various parts and details without departing from the scope of the invention.

What I claim is

1. A process for maintaining a graft or flap for animals viable for a period of time before surgical use comprising:
   (1) initially providing a fluid including a source of oxygen;
   (2) thereafter providing a graft or flap;
   (3) thereafter placing at least one artificial capillary tube into said graft or flap, said tube being formed of a material permitting said fluid to perfuse therethrough; and
   (4) then flowing said fluid first through said tube and then perfusing said fluid within said graft or flap;
   the quantity of oxygen from said oxygen source, the number of capillary tubes, and the rate of flow of said fluid being so correlated for maintaining said graft or flap viable for a sufficient period of time thereby preventing necroses of said flap or graft prior to surgical use,
   said process including the additional step of surgically transplanting said graft or flap to a segment of a living body.

2. A process as recited in claim 1 wherein said perfusing continues during said transplanting step.

3. A process as recited in claim 2 including the step of removing said tube after surgery.

4. A process for maintaining a vascularized living cell tissue portion of an animal viable for a period of time after surgical implanting of said tissue portion in order to allow revascularization by the implanted host animal to sustain viability of said tissue portion thereafter by said implanted host animal, comprising the steps of:
   providing a fluid including humidified oxygen;
   surgically implanting said tissue portion in host animal;
   placing at least one artificial capillary having sides into said tissue portion, said capillary being formed of a material permitting said humidified oxygen to pass through said material of said sides of said tube; and
   providing means for flowing said fluid with said humidified oxygen through said capillary and perfusing said humidified oxygen through said sides out into said tissue;
   the quantity of said humidified oxygen, the number of capillary tubes, and the rate of flow of said fluid with said humidified oxygen being so correlated for maintaining said tissue portion viable for a sufficient period of time thereby preventing necroses of said tissue portion prior to revascularization of said tissue portion by the implanted host animal after the surgically implanting of said tissue portion in said host animal.

5. A process for maintaining an existing vascularized living cell tissue portion of an animal viable for a period of time after surgical implanting of said existing tissue portion in order to allow revascularization by the implanted host animal to sustain viability of said existing tissue portion thereafter by said implanted host animal, comprising the steps of:
   providing a fluid including humidified oxygen;
   surgically implanting said existing tissue portion in host animal;
   placing at least one artificial capillary having sides into said existing tissue portion, said capillary being formed of a material permitting said humidified oxygen to pass through said material of said sides of said tube; and providing means for flowing said fluid with said humidified oxygen through said capillary and perfusing said humidified oxygen through said sides out into said existing tissue portion;

the quantity of said humidified oxygen, the number of capillary tubes, and the rate of flow of said fluid with said humidified oxygen being so correlated for maintaining said existing tissue portion viable for a sufficient period of time thereby preventing necroses of said existing tissue portion prior to revascularization of said existing tissue portion by the implanted host animal after the surgically implanting of said tissue portion in said host animal;

each said capillary is placed in said existing tissue portion by threading it through an internal portion of said existing tissue portion, each said internal portion spaced from the sides of said existing tissue portion and from other internal portions, if any.

6. A process for maintaining an existing living natural graft for animals viable for a period of time before use comprising the steps:
  (1) humidifying a stream of oxygen with water;
  (2) introducing said humidified oxygen stream into a body of artificial blood to oxygenate said artifical blood;
  (3) placing a series of artificial capillary into said graft in contact with the internal cells of said graft, and
  (4) feeding said oxygenated artificial blood through said artificial capillaries and then through said graft, said artificial capillaries permitting perfusion of oxygenated artificial blood into said graft for the diffusion distance of said artificial blood to maintain life in said graft, without requiring use of the animal's capillaries.

7. A process as recited in claim 6 wherein said oxygen stream includes carbon dioxide.

8. A process as recited in claim 6 wherein said artificial blood is a fluorocarbon emulsion.

9. A process as recited in claim 8 wherein said fluorocarbon emulsion is Fluorosol.

10. A process as recited in claim 6 wherein the artificial capillary is a semi-permeable membrane or matrix.

11. A process as recited in claim 10 wherein the semi-permeable membrane is a thin walled cellulose membrane or matrix.

12. A process as recited in claim 11 wherein said cellulose membrane or matrix includes thousands of capillary size tubules.

13. A process as recited in claim 12 wherein said tubules have an internal diameter of about 200 microns and a wall thickness of about 30 microns.

14. A process as recited in claim 11 wherein said membrane or matrix is disposed in an olefin tubular semi-permeable membrane.

15. A process as recited in claim 14 wherein said olefin is polyethylene and said polyethylene tubing functions as an artificial capillary or vein for delivering the artificial blood.

16. A process as recited in claim 6 wherein the living cell structure is a flap or graft for use in a surgical process.

17. A process as recited in claim 15 wherein the living cell structure is a flap or graft further including the step of suturing said polyethylene to the flap.

18. A process as recited in claim 6 further including the step of pumping the perfused artificial blood from said cell graph to said body of artificial blood as a recycle stream.

19. A process as recited in claim 7 wherein the oxygen/carbon dioxide is 95% oxygen to 5% carbon dioxide.

20. A process for maintaining an existing surgical flap or graft viable comprising the steps of:
  (a) introducing a gaseous stream of about 95% oxygen and about 5% carbon dioxide into a body of water to humidify said gaseous stream;
  (b) oxygenating a body of Fluorosol artificial blood by introducing said humidified gaseous stream into and below the surface of said body of Fluorosol;
  (c) providing a tubular semi-permeable membrane of polyethylene;
  (d) inserting a cellulose matrix or membrane including tubules of micron size into said polyethylene membrane;
  (e) securing said polyethylene containing said cellulose to said flap or graft; and
  (f) perfusing said Fluorosol artificial blood first through said polyethylene containing said cellulose matrix and then through said flap or graft;
  (g) whereby said flap or graft is maintained viable for about seven days for use in a surgical process.

21. A process as set forth in claim 6 including the steps of:
placing a plurality of said artificial capillary through an intermediate portion of said graft structure in the plane of said graft structure at intervals approximately equal to the transverse diffusion distance of said artificial blood from said artificial capillary placed in said intermediate portion to maintain life of said graft structure.

22. A process as set forth in claim 21 including the steps of:
placing said graft structure in place on an animal and maintaining perfusing of said oxygenated artificial blood through said artificial capillary to temporarily maintain life in said graft structure placed on the animal without use of micro surgery to connect recipient vessels.

23. A process for maintaining an existing living natural tissue cell graft for animals after severance from a host animal for transplantation to a recipient bed for a period of time sufficient to allow the recipient bed to revascularize the living natural tissue cell graft, said process utilizing a circulatory system in direct contact with an intermediate portion of said living natural tissue cell graft for perfusing and nourishing said living natural tissue cell graft to be transplanted, comprising the steps of:
  a. preparing said living natural tissue cell graft by severing said living natural tissue cell graft from a host animal;
  b. providing at least one artificial capillary means having two ends for transporting oxygen into said artificial capillary means and for allowing said oxygen to move out of said artificial capillary means and into said living natural tissue cell graft for sustaining viability;
  c. placing after severing at least one artificial capillary means for direct contact with said intermediate portion of said living natural tissue cell graft through said intermediate portion to be transplanted;
  d. placing the two ends of each said artificial capillary in an accessible position;
  e. humidifying a stream of oxygen with water;

f. introducing said humidified stream into a body of artificial blood to oxygenate said artificial blood;
g. providing an external circulatory system and connecting said external circulatory system to the ends of each said artificial capillary means for perfusing dissipation of oxygen and to nourish said intermediate portion of said living natural tissue cell graft;
h. profusing said oxygenated artificial blood through said artificial capillary portion to provide a diffusion distance from said artificial capillary means and through the walls of said artificial capillary means and through the living natural tissue cell graft which maintains the viability of the living natural tissue cell graft whereby the requirement of vascularization of the tissue cell structure by a pedicle is eliminated and the vascularization by microsurgery to the recipient animal is eliminated.

* * * * *